United States Patent
Okabe et al.

(10) Patent No.: US 9,884,725 B2
(45) Date of Patent: Feb. 6, 2018

(54) SPECIMEN TRANSPORT DEVICE, SPECIMEN PRETREATMENT SYSTEM, ANALYSIS SYSTEM, AND SPECIMEN TESTING AUTOMATION SYSTEM

(71) Applicant: HITACHI HIGH-TECHNOLOGIES CORPORATION, Tokyo (JP)

(72) Inventors: Shugo Okabe, Tokyo (JP); Tatsuya Fukugaki, Tokyo (JP); Shinji Azuma, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 11 days.

(21) Appl. No.: 15/028,207

(22) PCT Filed: Dec. 10, 2014

(86) PCT No.: PCT/JP2014/082607
§ 371 (c)(1),
(2) Date: Apr. 8, 2016

(87) PCT Pub. No.: WO2015/093353
PCT Pub. Date: Jun. 25, 2015

(65) Prior Publication Data
US 2016/0251164 A1 Sep. 1, 2016

(30) Foreign Application Priority Data
Dec. 19, 2013 (JP) .................................. 2013-261955

(51) Int. Cl.
*B65G 23/24* (2006.01)
*B65G 23/10* (2006.01)
(Continued)

(52) U.S. Cl.
CPC ............. *B65G 23/24* (2013.01); *B65G 15/12* (2013.01); *B65G 23/10* (2013.01); *B65G 23/28* (2013.01);
(Continued)

(58) Field of Classification Search
CPC ........ B65G 15/12; B65G 23/10; B65G 23/24; B65G 23/28; B65G 23/34; B65G 23/44;
(Continued)

(56) References Cited

U.S. PATENT DOCUMENTS 5,605,218 A    2/1997  von Froreich
6,024,204 A *  2/2000  van Dyke, Jr. ........ G01N 35/04
                                                          198/379
(Continued)

FOREIGN PATENT DOCUMENTS

CH     695 380 A5    4/2006
CN     20309452 U    7/2013
(Continued)

OTHER PUBLICATIONS

International Search Report of PCT/JP2014/082607 dated Mar. 31, 2015.
(Continued)

*Primary Examiner* — Gerald McClain
*Assistant Examiner* — Keith R Campbell
(74) *Attorney, Agent, or Firm* — Mattingly & Malur, PC

(57) ABSTRACT

A plurality of transport lines having driving belts are driven to transport specimen racks on which a specimen container is disposed. A single driving motor having a rotating shaft, a shaft for transmitting power of the driving motor, drives the driving belt and a plurality of pulleys transmit rotation of the shaft to the belts to drive the belts.

5 Claims, 4 Drawing Sheets

TRANSPORT DIRECTION

(51) Int. Cl.
  *B65G 23/28* (2006.01)
  *B65G 35/06* (2006.01)
  *G01N 35/04* (2006.01)
  *B65G 15/12* (2006.01)
  *B65G 23/44* (2006.01)

(52) U.S. Cl.
  CPC .............. *B65G 23/44* (2013.01); *B65G 35/06* (2013.01); *G01N 35/04* (2013.01); *G01N 2035/0482* (2013.01)

(58) Field of Classification Search
  CPC ........ B65G 35/06; G01N 35/04; G01N 35/06; G01N 2035/0482; G01N 2035/0484; G01N 2035/0486; G01N 2035/0487
  See application file for complete search history.

(56) References Cited

U.S. PATENT DOCUMENTS

| | | | | |
|---|---|---|---|---|
| 6,202,829 | B1* | 3/2001 | van Dyke, Jr. | ........ G01N 35/04 198/349.6 |
| 7,425,305 | B2* | 9/2008 | Itoh | .................... G01N 35/0099 422/547 |
| 8,322,510 | B2* | 12/2012 | Pedrazzini | ....... G01N 35/00732 198/346.2 |
| 9,638,710 | B2* | 5/2017 | Pedrazzini | ............. G01N 35/02 |
| 9,651,571 | B2* | 5/2017 | Sasaki | ................... G01N 35/04 |
| 2012/0177547 | A1 | 7/2012 | Fukugaki et al. | |
| 2015/0122614 | A1* | 5/2015 | Dumitrescu | ........ B65G 54/025 198/570 |
| 2015/0177267 | A1* | 6/2015 | Oonuma | ................ G01N 35/04 198/339.1 |

FOREIGN PATENT DOCUMENTS

| | | |
|---|---|---|
| DE | 35 14 716 A1 | 10/1986 |
| JP | 61-180161 A | 8/1986 |
| JP | 04-286529 A | 10/1992 |
| JP | 07-234228 A | 9/1995 |
| JP | 07-237724 A | 9/1995 |
| JP | 08-104408 A | 4/1996 |
| JP | 09-124125 A | 5/1997 |
| JP | 2000-146774 A | 5/2000 |
| WO | 2011/040197 A1 | 4/2011 |

OTHER PUBLICATIONS

Extended European Search Report received in corresponding European Application No. 14871702.8 dated Jul. 12, 2017.

* cited by examiner

[FIG. 1]
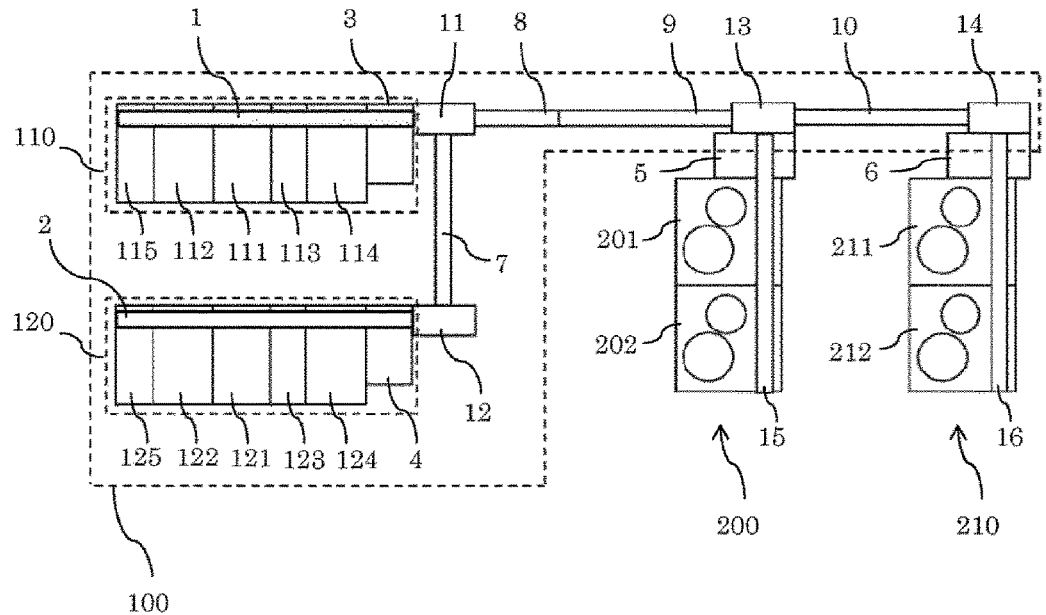
[FIG. 2]
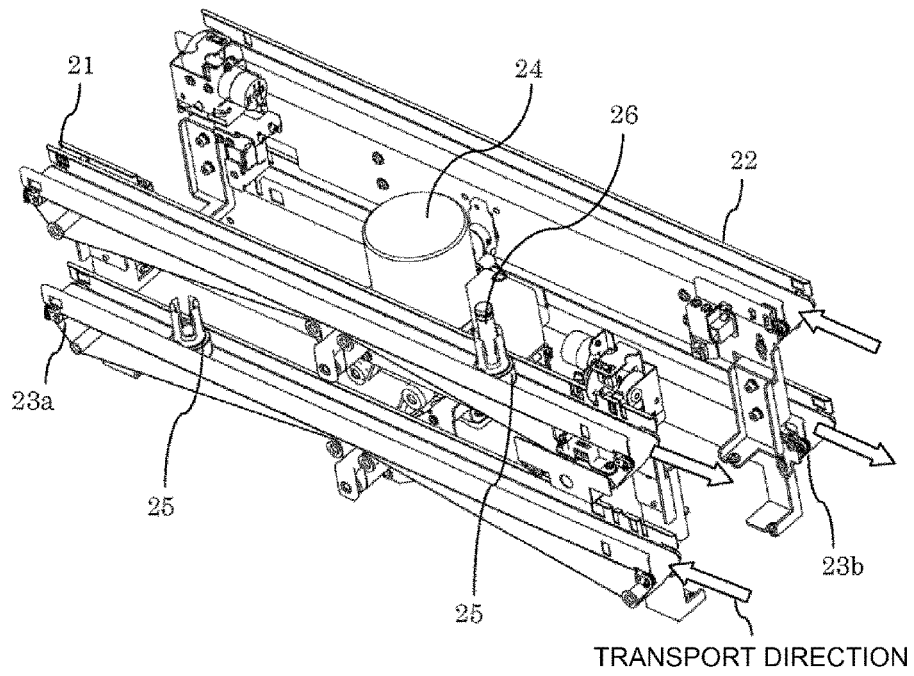
TRANSPORT DIRECTION

[FIG. 3]
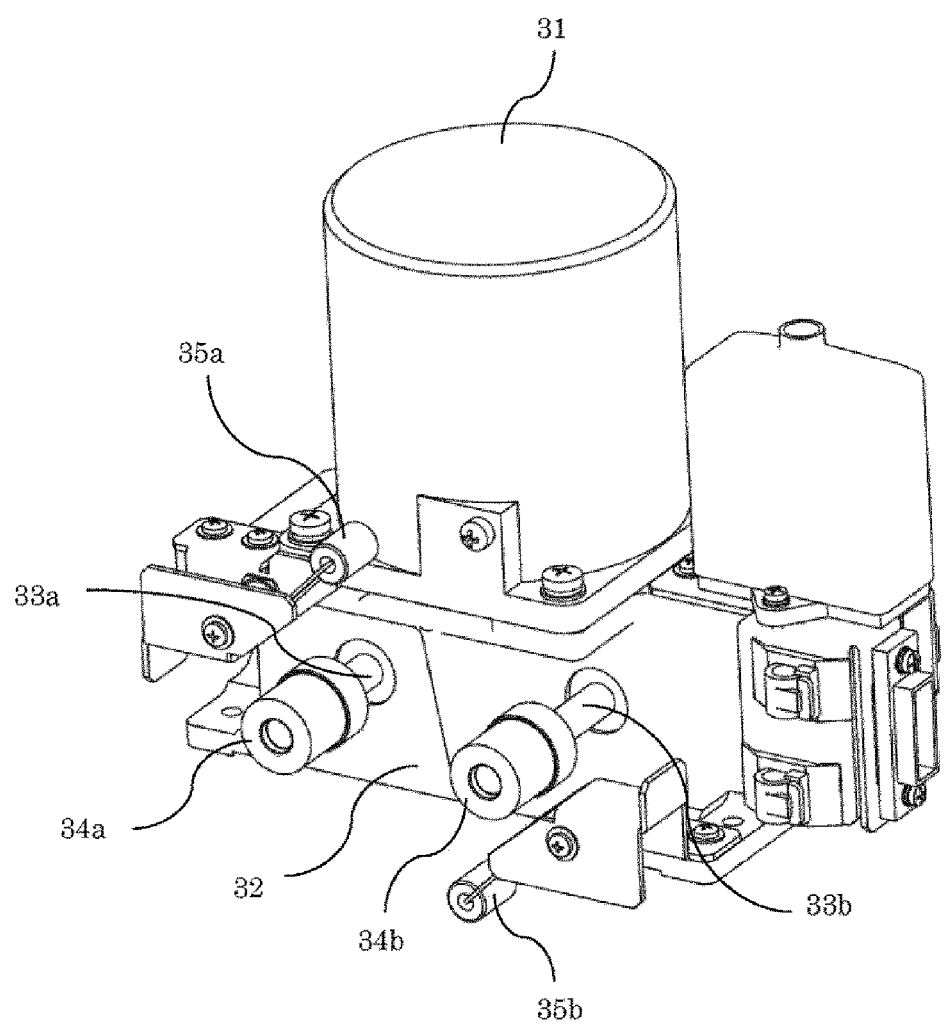

[FIG. 4]
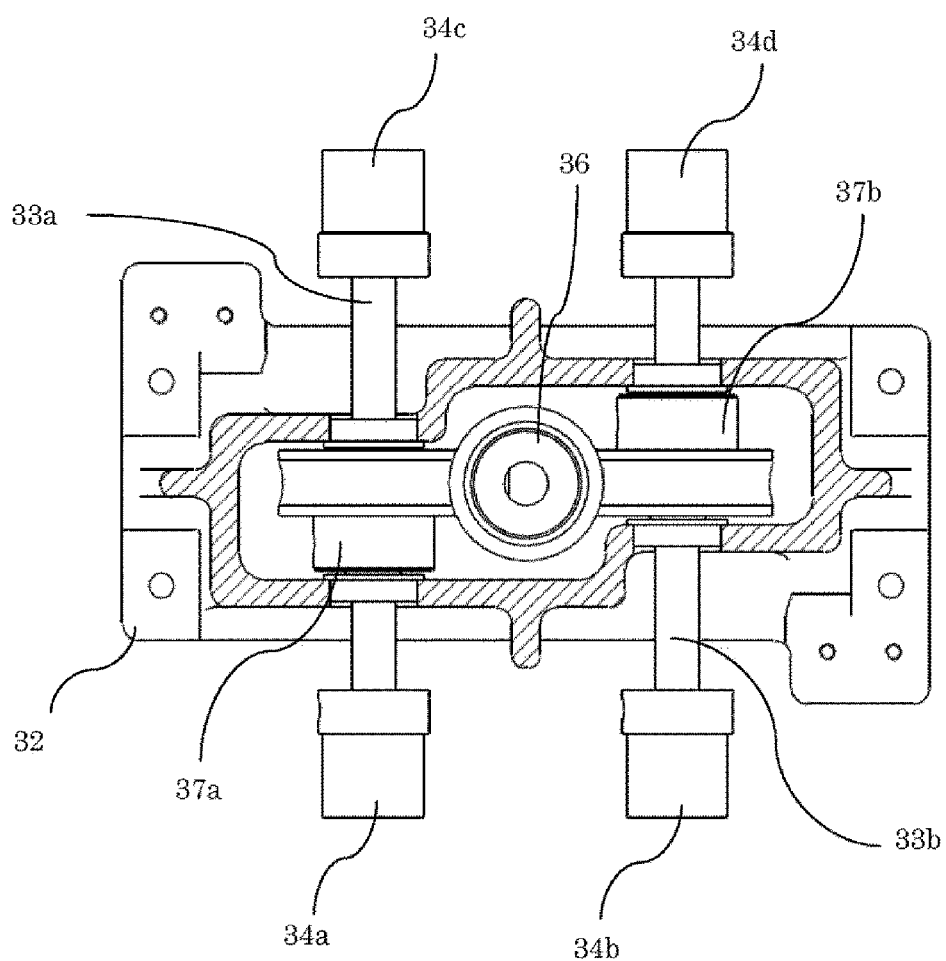

[FIG. 5]
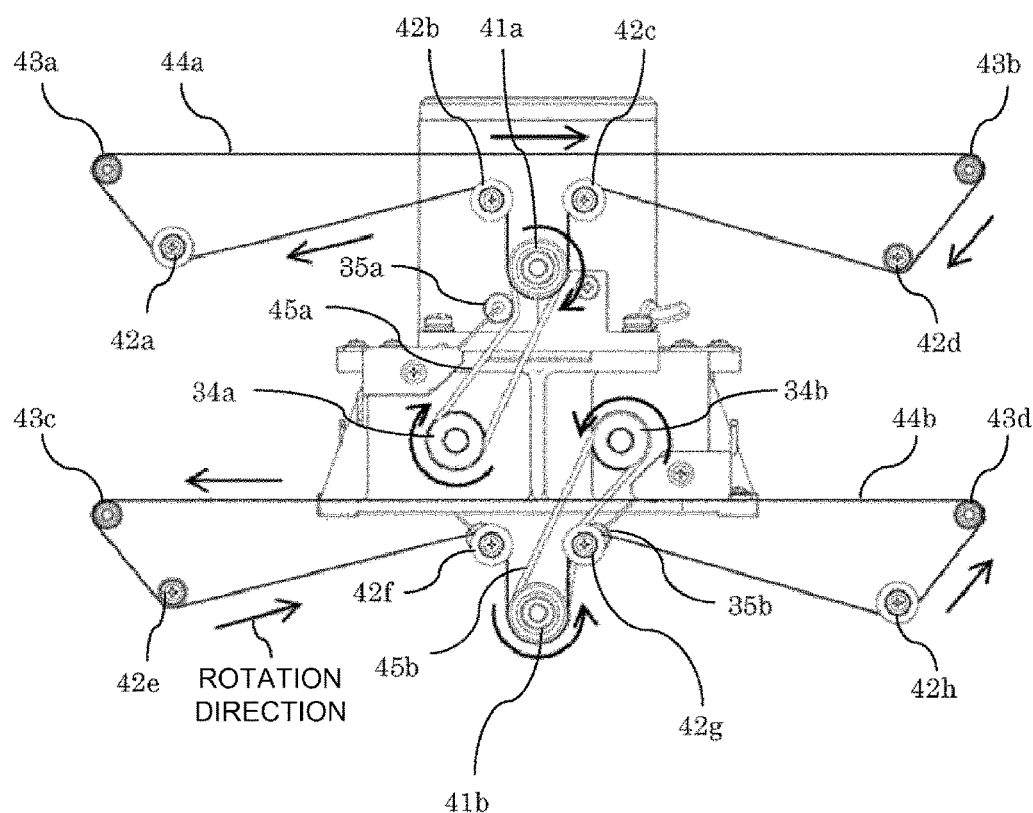

SPECIMEN TRANSPORT DEVICE, SPECIMEN PRETREATMENT SYSTEM, ANALYSIS SYSTEM, AND SPECIMEN TESTING AUTOMATION SYSTEM

TECHNICAL FIELD

The present invention relates to a technique for transporting specimen containers by driving a plurality of transport lines in parallel.

BACKGROUND ART

One background art in this technical field is WO2011/040197 (PTL 1). PTL 1 discloses as follows: "In the case where specimen racks are moved in a loop and are repeatedly used in a system in order to prevent an increase in size of a device and complication thereof, a processing speed decreases due to intersection of transport lines, and, in order to prevent such intersection, a complicated mechanism such as an elevator mechanism or a robot hand mechanism has been needed. Empty rack transport lines are disposed at lower positions so as to be independent from a main transport line, an emergency passing line, and a return line, and a rack stocker provided between a storing module and a feeding module is connected to the empty rack transport lines by transport lines inclined in the rack stocker. With this, the intersection of the transport lines is avoided, and therefore empty racks can be continuously supplied and collected. As a result, the intersection of the transport lines can be prevented with a simple configuration without increasing the size of the device or complicating the device, and the empty racks can be continuously supplied and collected without reducing a processing capacity. In addition, it is possible to provide a specimen testing automation system that is highly expandable in accordance with a scale of facilities".

CITATION LIST

Patent Literature

PTL 1: WO2011/040197

SUMMARY OF INVENTION

Technical Problem

In the above technique disclosed in PTL 1, the number of power sources (motors) for driving transport lines are increased in accordance with diversification/multiplication of the transport lines. Therefore, increase in power consumption caused by driving a large number of motors cannot be avoided.

Solution to Problem

The invention of the present application which has been made in view of the above problem is as follows. Specifically, the invention drives a plurality of transport lines for driving belts to transport specimen racks on which a specimen container is disposed, a single driving motor having a rotating shaft, a shaft for transmitting power of the driving motor, a plurality of pulleys for transmitting rotation of the shaft to the belts to drive the belts, and the belts of the plurality of transport lines by rotatably driving the pulleys.

Advantageous Effects of Invention

Because a mechanism for driving transport lines in the invention is a mechanism for driving a plurality of transport lines in parallel by using a single power source, the number of power sources needed to drive the transport lines is reduced. Therefore, it is possible to achieve low power consumption in a system.

BRIEF DESCRIPTION OF DRAWINGS

FIG. 1 is a system layout diagram including a specimen testing automation system and an analysis system according to an embodiment of the invention.

FIG. 2 is a perspective view of transport lines of a transport line unit in a specimen testing automation system according to this embodiment.

FIG. 3 is a perspective view of a transport line driving mechanism.

FIG. 4 is a gearbox cross-sectional view illustrating an internal structure of a gearbox.

FIG. 5 illustrates a driving principle of transport lines using a transport line driving mechanism.

DESCRIPTION OF EMBODIMENTS

Hereinafter, an example of the invention will be described with reference to drawings.

FIG. 1 is a layout diagram of a specimen testing automation system including a specimen preprocessing system and an analysis system according to this embodiment. Note that a system configuration is different depending on a scale of facilities, and therefore various combinations exist. Thus, one configuration will be described in this embodiment.

As illustrated in FIG. 1, a specimen testing automation system 100 is configured such that preprocessing systems 110 and 120 for performing necessary processing on a specimen prior to analysis thereof and a plurality of (two in this example) analysis systems 200 and 210 for performing analysis processing of the specimen that has been preprocessed are connected by transport line units 7, 8, 9, and 10. Note that, in the invention, a device including the above specimen preprocessing systems 110 and 120, the analysis systems 200 and 210, and the transport line units 7 to 10, the device having a function of transporting a specimen, is defined as a specimen transport device.

The preprocessing units 110 and 120 in the specimen testing automation system 100 include: transport lines 1 and 2 for transporting a specimen rack on which one or a plurality of specimen containers containing a specimen are mountable; and specimen feeding modules 111 and 121, specimen storage modules 112 and 122, and processing modules 113, 114, 115, 123, 124, and 125 placed along the transport lines 1 and 2. Herein, the processing modules are, for example, a centrifugation module for performing centrifugation processing on a specimen, an opening module for opening a cap of an opening portion of a specimen container, a dispensing module for dispensing a specimen in a specimen container to a plurality of child specimen containers, and a closing module for closing a cap of an opening portion of a container. In addition, any other publicly-known processing module may be provided.

In each of the specimen feeding modules 111 and 121, a specimen container is fed by a feeding tray in which specimen containers are arrayed. The fed specimen container is held and lifted by a specimen chuck mechanism (not illustrated), is mounted on an empty specimen rack, and is then transported to another processing module via the preprocessing unit transport line 1 or 2. Also in each of the specimen storage modules 112 and 122, a storage tray in which specimen containers that have been processed or analyzed can be arrayed is provided, and the specimen container is held and lifted by a specimen chuck mechanism (not illustrated) from the specimen rack transported via the preprocessing unit transport lines 1 or 2 and is stored in the storage tray. At this time, the specimen rack from which the specimen container has been removed is transported again to the specimen feeding module 111 or 121, and the next specimen container that is newly fed is mounted thereon.

Specimen racks taken out by the preprocessing units 110 and 120 are transported to the analysis systems 200 and 210 placed downstream via divergence transport line units 11, 12, 13, and 14 and the transport line units 7, 8, 9, and 10. Note that, in the case where a delay is caused in the transport line units or the analysis systems or in the case where a part of analysis units cannot perform analysis, the specimen racks are temporarily evacuated to any of buffer units 3, 4, 5, and 6.

In the case where the specimen rack is brought in the analysis system, the specimen rack is brought in any of analysis modules 201, 202, 211, and 212 that can measure a requested analysis item via transport line 15 or 16, and analysis is performed. The specimen rack that has been analyzed is caused to return to the preprocessing systems 110 or 120 again via the transport lines 7, 8, 9, and 10 and is then stored in the specimen storage module 112.

FIG. 2 is a perspective view of transport lines forming the transport line units 7 to 10 in the specimen testing automation system 100 according to this embodiment. Each transport line unit may be configured by connecting a plurality of transport lines in accordance with a length thereof. The preprocessing unit transport lines 1 and 2 for transporting specimen containers in the preprocessing units 110 and 120 and the transport lines 15 and 16 for transporting specimen containers in the analysis systems 200 and 210 may also have a similar configuration.

The transport lines forming the transport line units 7 to 10 include a main transport line 21 for transporting a specimen rack to be brought in the analysis system from the preprocessing unit, a return line 22 for transporting a specimen rack to return to the preprocessing unit from the analysis system, an empty rack transport line 23 for transporting an empty specimen rack on which no specimen container is mounted, the empty rack transport lines being placed at a stage lower than the main transport line 21 and the return transport line 22, and a transport line driving mechanism 24 for driving those lines. Each line includes a side wall for stably transporting a specimen rack and an endless belt that is rotatably driven, and, when the belt is driven in directions, a specimen rack mounted thereon is also driven.

Herein, for example, an empty specimen rack 25 from which a specimen container 26 has been removed by the specimen storage module is transported to the empty rack transport line 23 by a connection transport line (not illustrated) connecting the main transport line 21 and the empty rack transport line. The connection transport line is inclined to connect upper and lower transport lines.

The empty rack transport lines 23 are disposed to be in parallel with the main transport line 21 and the return line 22 and have the same length as that of the main transport line 21 and the return line 22 and are placed at a stage lower than the main transport line 21 and the return line 22. The empty rack transport lines 23 have the same line length as that of the main transport line 21 and the return line 22 to easily achieve expandability of a system (for example, to add or remove a processing module later). Note that the empty rack transport lines 23 are empty rack transport lines 23a and 23b herein, and the empty rack transport line 23a is provided immediately below the main transport line 21 and transports an empty specimen rack in a direction opposite to a direction of the main transport line 21. Similarly, the empty rack transport line 23b is provided immediately below the return line 22 and transports an empty specimen rack in a direction opposite to a direction of the return line 22.

FIG. 3 is a perspective view of the transport line driving mechanism 24 in the invention.

The transport line driving mechanism 24 causes a gearbox 32 including worm gears to change a power direction of power of a driving motor 31 having a vertical direction as a rotation axis center, thereby transmitting the power to one or more (two in this example) shafts 33a and 33b. When the shafts 33a and 33b are rotated, timing pulleys 34 are rotated, and therefore belts are driven.

FIG. 4 is a gearbox 32 cross-sectional view illustrating an internal structure of the gearbox. The cross-sectional view illustrates a state of the perspective view of FIG. 3 seen from the above. A worm 36 attached to a rotating shaft of the driving motor 31 and worm wheels 37 attached to the shafts 33 are engaged with each other to transmit power of the driving motor 31 to the shafts 33a and 33b. Note that the shafts 33a and 33b are adjusted to be rotated in opposite directions. Rotation of the shafts 33a and 33b is transmitted to timing pulleys 34a, 34b, 34c, and 34d.

FIG. 5 illustrates a driving principle of transport lines using the transport line driving mechanism 24, which exemplifies the main transport line 21 and the empty rack transport line 23a in the transport line units 7 to 10. A similar structure is also provided on the side of the return line 22 and the empty rack transport line 23b.

Herein, in each transport line, a belt 44 disposed along a driving pulley 41, driven pulleys 42, and tail pulleys 43 is rotated, and the specimen rack 26 is mounted on an upper surface of the belt 44 and is moved. The driving pulley 41 is connected to the timing pulley 34 attached to the shaft 33 of the driving mechanism 24 by a timing belt 45, and power from the driving motor 31 is transmitted to the belt 44. In this example, the timing pulleys 34a and 34b are rotated in opposite directions, and therefore the driving pulleys 41a and 41b are also rotated in opposite directions. Thus, driving directions of the belts can also be opposite to each other. A belt tension of the timing belt 45 can be adjusted by adjusting a position of a tension adjustment roller 35a.

Although FIG. 5 only illustrates one side, a similar configuration is provided on the other side. Therefore, the main transport line 21 is driven by the timing pulley 34a connected to the shaft 33a and the empty rack transport line 23b is driven by the timing pulley 34c, and the empty rack transport line 23a is driven by the timing pulley 34b connected to the shaft 33b and the return line 22 is driven by the timing pulley 34d.

With the above operation principle, two shafts 32a and 32b can be driven by the single driving motor 31, and therefore four transport lines can be simultaneously driven. Further, a transport direction of each transport line can be appropriately adjusted as necessary. That is, in this example, the main transport line 21 and the empty rack transport line 23b can be driven by power transmitted from the shaft 33a, and the return line 22 and the transport line 23a can be driven by power transmitted from the shaft 33b. Therefore, even in the case where the number of transport lines is increased, the number of motors for driving those transport lines can be reduced, which results in preventing increase in power consumption. Note that ideas of the invention are not limited to the above combination, and it is possible to arbitrarily change transport directions by changing connection between the driving pulleys 41 and the timing belts 45. In addition, when the number of worm wheels 37 to be attached to the driving motor 31 is adjusted, it is possible to change the number of transport lines to be driven. In the case of a structure including only a worm wheel 37*a*, two transport lines can be driven by the single driving motor 31. When three or more worm wheels 37 are attached to the driving motor 31, six or more transport lines can be driven by the single driving motor.

In the above example, the transport lines of the transport line units 7 to 10 which are the simplest forms have been described. However, in the case where a plurality of transport lines disposed in parallel exist in the preprocessing units 110 and 120, the buffer units 3 to 6, the divergence transport line units, and the analysis systems 200 and 210, the invention can be implemented. In this case, the main transport line 21 serves as a line for transporting the specimen 26 to a processing device in each preprocessing unit or to an analysis module in each analysis system, and the return line 22 serves as a transport line for moving the specimen 26 in a loop in the system.

REFERENCE SIGNS LIST

1, 2 preprocessing unit transport line
3, 4, 5, 6 buffer unit
7, 8, 9, 10 transport line unit
11, 12, 13, 14 divergence transport line unit
21 main transport line
22 return line
23 empty rack transport line
24 transport line driving mechanism
25 specimen rack
26 specimen
31 driving motor
32 gearbox
33 shaft
34 timing pulley
35 tension adjustment roller
36 worm
37 worm wheel
41 driving pulley
42 driven pulley
43 tail pulley
44 belt
45 timing belt
100 specimen testing automation system
110, 120 preprocessing unit
111, 121 specimen feeding module
112, 122 specimen storage module
113, 114, 115, 123, 124, 125 processing module
200, 210 analysis system
201, 202, 211, 212 analysis module

The invention claimed is:

1. A specimen transport device, comprising:
a main transport line, having a first belt, for transporting, in one direction, a specimen to be processed,
a return line, having a second belt, for transporting, in a direction opposite to the direction of the main transport line, a specimen that has been processed,
a first empty rack transport line, having a third belt, for performing transport in the direction opposite to the direction of the main transport line, the first empty rack transport line disposed lower than the main transport line,
a second empty rack transport line, having a fourth belt, for performing transport in a direction opposite to the direction of the return line, the second empty rack transport line disposed lower than the return line,
a single driving motor,
a first shaft transmitting power of the single driving motor to the main transport line,
a second shaft transmitting power of the single driving motor to the return line, the second shaft being rotated in a direction opposite to a direction of the first shaft,
a first pulley driving the main transport line, the first pulley being provided on the first shaft,
a second pulley driving the first empty rack transport line, the second pulley being provided on the first shaft,
a third pulley driving the return transport line, the third pulley being provided on the second shaft, and
a fourth pulley driving the second empty rack transport line, the fourth pulley being provided on the second shaft,
wherein the first belt of the main transport line, the second belt of the return transport line, the third belt of the first empty rack transport line, and the fourth belt of the second empty rack transport line are rotatably driven by the first pulley, the second pulley, the third pulley, and the fourth pulley, respectively.

2. The specimen transport unit according to claim 1, further comprising:
a timing belt and a roller applying tension to the timing belt.

3. A specimen preprocessing system, comprising:
the specimen transport device according to claim 1;
a specimen feeding module for feeding a specimen to be processed to the system;
a specimen storage module for storing a specimen that has been processed; and
a processing module for performing predetermined processing on a fed specimen, wherein
the specimen transport device connects the specimen feeding module, the specimen storage module, and the processing module.

4. An analysis system, comprising:
the specimen transport device according to claim 1; and
a plurality of analysis modules each configured to measure a requested analysis item of a transferred specimen,
wherein the specimen transport device connects the plurality of analysis modules.

5. A specimen testing automation system, comprising:
the specimen transport device according to claim 1;
a specimen preprocessing system including a specimen feeding module for feeding a specimen to be processed to the system, a specimen storage module for storing a specimen that has been processed, and a processing module for performing predetermined processing on a fed specimen; and
an analysis system including a plurality of analysis modules for performing analysis processing on the specimen, wherein
the specimen transport device connects the specimen preprocessing system and the analysis system.

* * * * *